US012788959B2

(12) United States Patent
Dowell et al.

(10) Patent No.: US 12,788,959 B2
(45) Date of Patent: Nov. 10, 2026

(54) BARBED STOPCOCK AND SECUREMENT CLIPS FOR MEDICAL TUBING

(71) Applicant: Cook Medical Technologies LLC, Bloomington, IN (US)

(72) Inventors: Angela R. Dowell, Lafayette, IN (US); Shaun A. Tanner, West Lafayette, IN (US); Adam McGoff, Indianapolis, IN (US); Andrew P. Isch, Lafayette, IN (US); Kathryn R. Hardert, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 227 days.

(21) Appl. No.: 18/541,318

(22) Filed: Dec. 15, 2023

(65) Prior Publication Data

US 2024/0198077 A1 Jun. 20, 2024

Related U.S. Application Data

(60) Provisional application No. 63/433,841, filed on Dec. 20, 2022.

(51) Int. Cl.

| | |
|---|---|
| ***A61M 39/22*** | (2006.01) |
| ***A61M 1/04*** | (2006.01) |
| ***F16K 11/085*** | (2006.01) |
| ***F16K 27/06*** | (2006.01) |
| ***F16L 33/035*** | (2006.01) |
| *A61M 25/02* | (2006.01) |
| *A61M 39/10* | (2006.01) |

(52) U.S. Cl.

CPC .............. *A61M 39/22* (2013.01); *A61M 1/04* (2013.01); *F16K 11/0853* (2013.01); *F16K 27/065* (2013.01); *F16L 33/035* (2013.01); *A61M 2025/0286* (2013.01); *A61M 2039/1077* (2013.01); *A61M 2039/229* (2013.01)

(58) Field of Classification Search

CPC ............ A61M 39/22; A61M 2039/229; F16K 27/065

See application file for complete search history.

(56) References Cited

U.S. PATENT DOCUMENTS

| | | | | |
|---|---|---|---|---|
| 5,466,228 | A * | 11/1995 | Evans ................. | F16K 11/0853 604/32 |
| 6,457,488 | B2 | 10/2002 | Loo | |
| 7,921,874 | B2 | 4/2011 | Tekulve et al. | |

(Continued)

FOREIGN PATENT DOCUMENTS

| | | | |
|---|---|---|---|
| EP | 2954913 | A1 | 12/2015 |
| JP | H07236696 | A * | 9/1995 |
| WO | WO2021191715 | A1 | 9/2021 |

OTHER PUBLICATIONS

JPH07236696A machine translation (Year: 1995).*

(Continued)

*Primary Examiner* — Michael R Reid

(74) *Attorney, Agent, or Firm* — Crowell & Moring LLP

(57) ABSTRACT

A drainage system, including a stopcock and a clip. The stopcock includes a base and a barbed adapter extending from the base. The barbed adapter includes a shaft portion and a barbed portion. The clip includes a first grip and a second grip. The clip is configured to secure at least one tubing to the stopcock.

5 Claims, 6 Drawing Sheets

(56) References Cited

U.S. PATENT DOCUMENTS

| | | | | |
|---|---|---|---|---|
| 9,061,122 | B2 | 6/2015 | Bierman et al. | |
| 9,995,405 | B2 * | 6/2018 | Duncan | F16K 11/0853 |
| 10,004,890 | B2 * | 6/2018 | Liu | A61M 39/223 |
| 10,627,030 | B2 | 4/2020 | Lewis et al. | |
| 2008/0067462 | A1 | 3/2008 | Miller et al. | |
| 2010/0249727 | A1 | 9/2010 | Thorne, Jr. et al. | |
| 2018/0318554 | A1 | 11/2018 | Karim et al. | |
| 2018/0360635 | A1 | 12/2018 | Wojcik et al. | |
| 2019/0015627 | A1 | 1/2019 | Hall et al. | |
| 2019/0336745 | A1 | 11/2019 | Mujwid et al. | |
| 2020/0030578 | A1 | 1/2020 | Andino et al. | |
| 2020/0108242 | A1 | 4/2020 | Stankowski et al. | |
| 2021/0247008 | A1 | 8/2021 | Sillitoe et al. | |
| 2023/0008738 | A1 * | 1/2023 | Rothert | A61M 39/20 |

OTHER PUBLICATIONS

3-Way Stopcock, Female Luer Lock, Barb, Tubing Port with One-Way Air Check Valve,99895, Qosina, 2021, 2 pages, Retrieved from the Internet: https://www.qosina.com/3-way-stopcock-female-luer-lock-barb-tubing-port-with-one-way-air-check-valve-99895.

Nalgene 3-Way Stopcock with 2mm Bore, U.S. Plastic Corp., 5 pages, Retrieved from the Internet:https://www.usplastic.com/catalog/item.aspx?itemid=32029&gclid=EAIaIQobChMlpafh9dS28wIVY2pvBB1xQA7XEAKYBCABEgJG5_D_BwE.

Masterflex Adapter Fittings, Sanitary Clamps to Hose Barb, Straight, 2 pages, Retrieved from the Internet: https://www.fishersci.se/shop/products/polypropylene-sanitary-barbed-adapter-3/11726088, dated Jan. 18, 2024.

* cited by examiner

BARBED STOPCOCK AND SECUREMENT CLIPS FOR MEDICAL TUBING

CROSS-REFERENCE TO RELATED APPLICATIONS

This application claims priority from U.S. Provisional Application No. 63/433,841, filed Dec. 20, 2022, which is hereby fully incorporated by reference herein in its entirety.

TECHNICAL FIELD

The present embodiments relate generally to medical devices, and more particularly, to medical devices for drainage.

BACKGROUND

The accumulation of air or fluid in the pleural space can prevent the lung(s) from expanding fully during breathing. In some cases, this is life-threatening. Current British Thoracic Society guidelines recommend that initial treatment of pleural disease typically involves the placement of a drainage catheter in order to drain the air and/or excess fluid. Pleural drainage devices require secure and airtight connections to suction devices in order to effectively drain the pleural space. Current pleural drainage product offerings typically have hubs with a conical shape or a luer-lock fitting. These options generally require the use of adapters to connect the drainage catheters to suction equipment that is necessary for drainage. Current product offerings rely on a friction fit between the catheter hub (or adapter) and the suction device. Tape is also widely used for improved securement.

Various styles of stopcocks are commonly used with a syringe to sample fluid from the pleural space, which is necessary for diagnostic workup. The stopcock+syringe is also used to flush the drain or to instill therapeutic fluids as a treatment option. However, commercially available stopcock options have more restrictive internal diameters than all large-bore drains and some small-bore drains.

SUMMARY

One general aspect of the present disclosure includes a drainage system, including: a clip including a first grip and a second grip; and a stopcock, which includes: a base, and a first barbed adapter extending from the base, the first barbed adapter including a first shaft portion and a first barbed portion, where the first grip is configured to fit over a first tubing coupled to the first barbed portion, and the second grip is configured to fit over the first shaft portion, such that the first tubing is secured to the stopcock via the clip.

Another general aspect of the present disclosure includes a drainage system, including: a clip including a first grip and a second grip; and a stopcock, which includes: a base, a first barbed adapter extending from the base, the first barbed adapter including a first shaft portion and a first barbed portion, and a second barbed adapter extending from the base, the second barbed adapter including a second shaft portion and a second barbed portion, where the first grip is configured to fit over a first tubing coupled to the first barbed portion, and the second grip is configured to fit over a second tubing coupled to the second barbed portion, such that the first tubing and the second tubing are secured to the stopcock via the clip.

Another general aspect of the present disclosure includes a stopcock, including: a base; a first barbed adapter extending from the base; a second barbed adapter extending from the base, where the first barbed adapter and the second barbed adapter are substantially 180 degrees apart; and a connection port extending from the base, where the connection port is substantially 90 degrees apart from the first barbed adapter and the second barbed adapter.

Another general aspect of the present disclosure includes a clip, including: a first grip including a first arm and a second arm; and a second grip including a third arm and a fourth arm, where the first arm and the second arm are spaced apart a first distance, the first distance being dimensioned such that the first grip fits snugly over a first medical tubing, where the third arm and the fourth arm are spaced apart a second distance, the second distance being dimensioned such that the second grip fits snugly over a second medical tubing, and where the first distance is greater than the second distance.

Another general aspect of the present disclosure includes a clip, including: a first grip including a first arm and a second arm; and a second grip including a third arm and a fourth arm, where the first arm and the third arm are connected via a first bar, where the second arm and the fourth arm are connected via a second bar, and where the second bar includes a bend.

Other systems, methods, features and advantages of the invention will be, or will become, apparent to one with skill in the art upon examination of the following figures and detailed description. It is intended that all such additional systems, methods, features and advantages be within the scope of the invention.

BRIEF DESCRIPTION OF DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION

Figure 1:
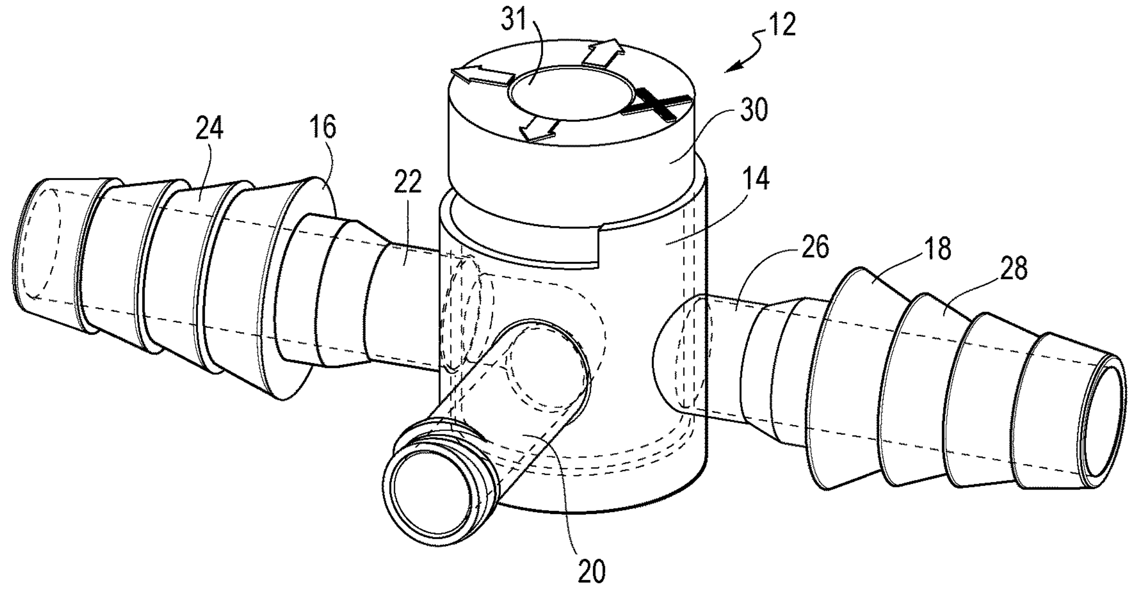
FIG. 1 is a perspective view of a stopcock according to an embodiment of the present invention, including a base and a plug disposed in the base.

Various aspects are described below with reference to the drawings in which like elements generally are identified by like numerals. The relationship and functioning of the various elements of the aspects may better be understood by reference to the following detailed description. However, aspects are not limited to those illustrated in the drawings or explicitly described below. It also should be understood that the drawings are not necessarily to scale (although certain drawings may be drawn to scale and relied upon as such), and in certain instances details may have been omitted that are not necessary for an understanding of aspects disclosed herein, such as conventional material, construction, and assembly.

For purposes of promoting an understanding of the presently disclosed embodiments, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the present application, the term "configured to" is used to describe structural limitations in a particular manner that requires specific construction to accomplish a stated function and/or to interface or interact with another component(s), and is not used to describe mere intended or theoretical uses. Relative terminology and broader terms such as "generally," "about," "substantially," and the like will be understood by those of skill in the art as providing clear and definite scope of disclosure and/or claiming. For example, the term "substantially 180 degrees apart" will be understood as not requiring exactly 180 degrees apart, but rather including that and functional equivalents.

Referring to FIGS. 1-12, various embodiments of a system 10 including a stopcock and at least one clip are shown. Although the system 10 will be described as a drainage system for use in a drainage procedure (e.g., pleural drainage), the system 10 may be used in other types of drainage procedure and may be used for other purposes, rather than drainage, to provide fluid communication between different tubing, without departing from the scope of the present invention. Features discussed below with respect to one embodiment of the drainage system 10 or any one of its components may be incorporated into other embodiments of the drainage system 10 or its components. Accordingly, similar features in different embodiments may not be repeated in detail.

Figure 2:
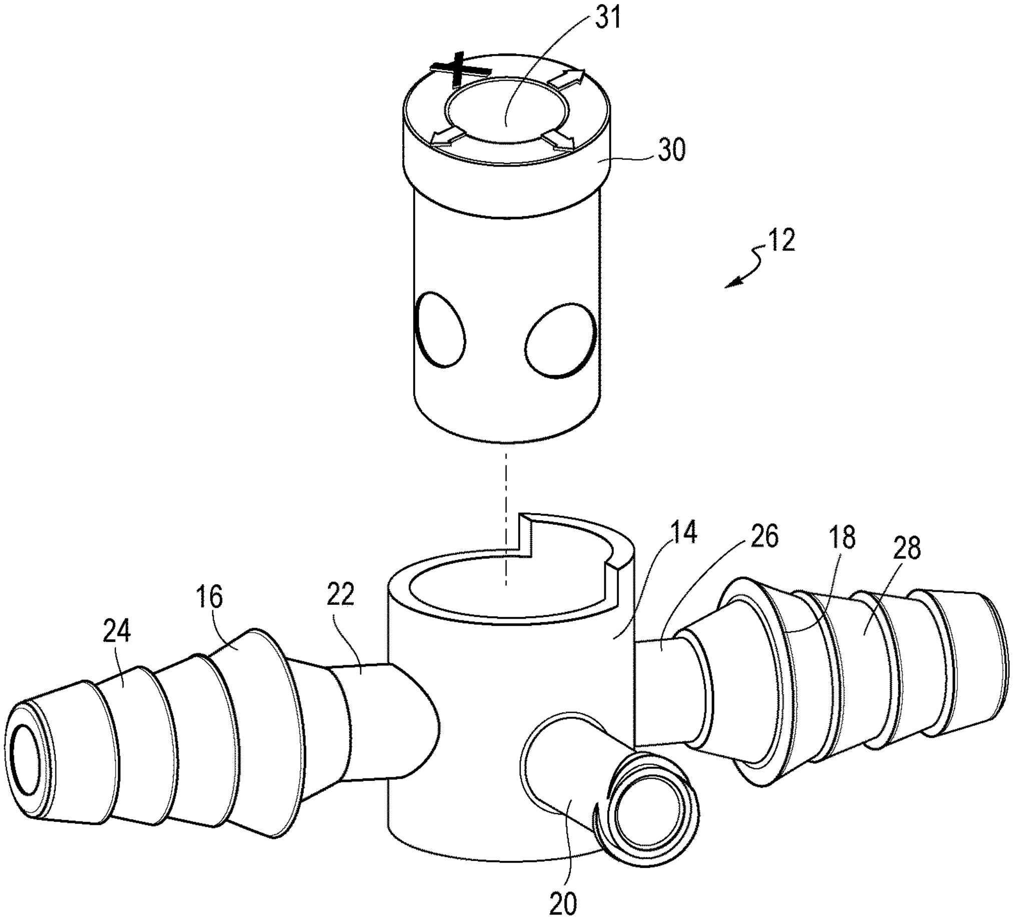
FIG. 2 is an exploded view of the stopcock of FIG. 1, showing separated base and plug.
Figure 3:
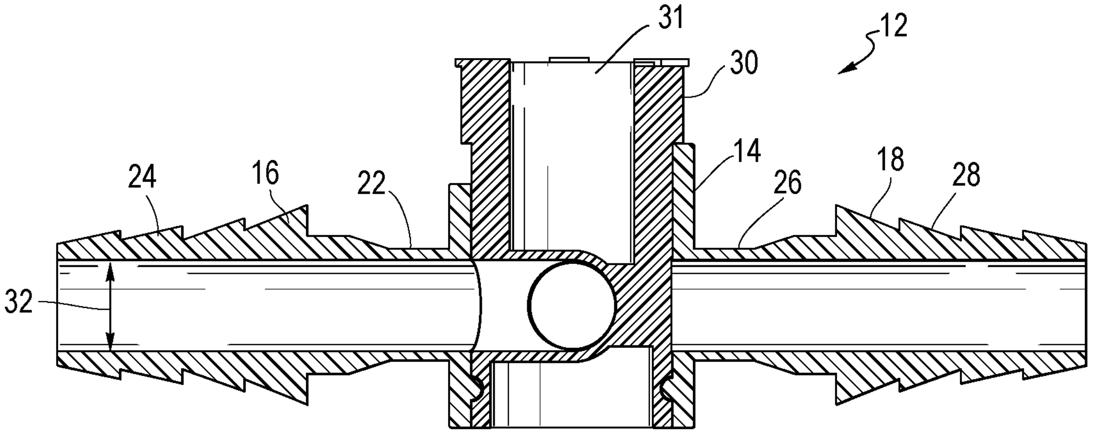
FIG. 3 is a cross-sectional view of the stopcock of FIG. 1.

Referring to FIGS. 1-3, an embodiment of a stopcock 12 (e.g., a three-way stopcock) is shown. The stopcock 12 includes a base 14, a first barbed adapter 16 extending from the base 14, and a second barbed adapter 18 extending from the base 14, where the first barbed adapter 16 and the second barbed adapter 18 are substantially 180 degrees apart. The stopcock 12 also includes a connection port 20 (e.g., a female luer lock; luer slip port) extending from the base 14, where the connection port 20 is substantially 90 degrees apart from the first barbed adapter 16 and the second barbed adapter 18. In some embodiments, the first barbed adapter 16, the second barbed adapter 18, and the connection port 20 may extend from the base 14 with other angles relative to each other, without departing from the scope of the present invention.

As shown in FIGS. 1-3, the first barbed adapter 16 includes a first shaft portion 22 and a first barbed portion 24, and the second barbed adapter 18 includes a second shaft portion 26 and a second barbed portion 28. The first and second barbed adapters 16 and 18 are configured such that tubing (e.g., medical tubing; conical shaped hub) may be coupled to the stopcock 12 via the first and second barbed adapters 16 and 18, as discussed in greater detail below. In some embodiments, the first barbed adapter 16 and the second barbed adapter 18 may have a constant inner diameter 32 (e.g., as shown in FIG. 3). In some embodiments, the first and second barbed adapters 16 and 18 may be configured to be compatible with most existing pliable conical hubs, adapters, and most existing vacuum tubing for chest drainage. The configuration of the stopcock 12 is advantageous for its compatibility with existing products for intended purposes (e.g., pleural drainage). The connection port 20 may be used for sampling fluid, flushing the drainage path, or instilling a therapeutic agent. The connection port 20 may be configured to be compatible with other extension tube luer fittings (e.g., including those currently on the market). While in the embodiment shown in the figures, the inner profile of the connection port 20 is generally a cylinder, in some embodiments, the inner profile of the connection port 20 is not a cylinder. The inner profile of the connection port 20 may have a taper, which is larger at the threaded distal end and smaller toward the center of the stopcock where the plug 30 rests. The taper may be compliant with standards pertaining to female luer taper (i.e. luer lock or luer slip) connections.

The stopcock 12 also includes a plug 30 rotatably disposed in the base 14 and configured to provide directional flow through the stopcock 12. In some embodiments, as shown in FIG. 2, at least a portion of the plug 30 may have a substantially cylindrical configuration. The arrows/structures of commercial stopcocks may snag doctor's/nurse's gloves, patient sheets or gowns, or other objects, and accidentally get repositioned. The configuration of the stopcock 12 in this application (e.g., the cylindrical configuration of the plug 30) requires more intentional positioning, which is advantageous for reducing unintentional repositioning. In some embodiments, the plug 30 may include a first non-word symbol indicating a no-flow position and a second non-word symbol indicating a flow position. For example, the plug 30 may have visual symbols of "T" and "X" indicating flow and no-flow positions, respectively, which is advantageous as it allows users to understand them without language barriers. The visual symbols may be colorized to provide background contrast and additional cognitive cues (e.g. red for stop and green for flow).

Moreover, ribbed or "coin edge" grip on the plug 30 allows for easy actuation while wearing medical gloves. The orientation of the barbed fittings/adapters of this stopcock, as compared to commercial 2-way and 3-way luer stopcocks, allows for an ergonomic hand hold during valve actuation, providing a more comfortable grip and stability during twisting of the valve mechanism (e.g., the plug 30) instead of relying on gripping attached tubes.

In some embodiments, the plug 30 may have rounded edges and a reduced profile to minimize discomfort to a patient. In some embodiments, the plug 30 and the base 14 may include corresponding detents for locking them together and/or preventing accidental rotation of the plug 30. Providing a physical hard-stop between the plug 30 and the base 14 of the stopcock prevents inadvertent over-rotation (e.g., preventing rotation of the plug more than 270 degrees) and minimizes the likelihood of use error that could result in patient harm. In some embodiments, the plug 30 and the base 14 may be mated with a semi-circular ridge, so that they can be easily paired during the manufacturing process. In some embodiments, as shown in FIGS. 1-3, for example, the plug 30 includes a blind bore 31 extending from the upper surface of the upper portion of the plug 30, along a longitudinal axis of the plug 30, to a position proximate the connection port 20.

In some embodiments, the stopcock 12 may be configured to have an inner diameter 32 (e.g., as shown in FIG. 3) that can accommodate both small bore drain (e.g., drainage catheter having an outer diameter less than 16 Fr) and large bore drain (e.g., drainage catheter having an outer diameter equal to or larger than 16 Fr), which is advantageous for allowing more versatile allowable flow through the stopcock 12. Specifically, accommodating a bore drain means that when a bore drain is connected to the stopcock 12 for drainage, the stopcock 12 does not substantially restrict flow due to the substantially continuous/same inner diameter 32 from the first barbed adapter 16 to the second barbed adapter 18 with a substantially matching/same inner diameter in the plug 30 when the flow is open to the first and the second barbed adapters. For example, the stopcock 12 may be configured to have an inner diameter 32 that can accommodate a 32 Fr drainage catheter, which has an inner diameter of 0.304"±0.002". In some embodiments, the stopcock 12 may be configured to connect either a small bore drain (e.g., 06 Fr drain) or a large bore drain (e.g., 24 Fr drain) to a vacuum tubing. For example, the large bore of the 24 Fr drain (having an inner diameter of 0.243") requires any attached hub/stopcock to have a comparable inner diameter for sufficient flow. Accordingly, as a non-limiting example, the stopcock 12 may be configured to have an inner diameter 32 that is between about 0.2" and about 0.30" (e.g., 0.223") which (unlike predicate devices) will accommodate both small and large bore drains. The term "about" is specifically defined herein to include the specific value referenced as well as a dimension that is within 15% of the dimension both above and below the dimension.

The ID ("inner diameter") of commercially available stopcocks is smaller than the OD ("outer diameter") of inserters (e.g., stiffeners, obturators, trocars, bougies) which are used to aid in the insertion of 14 Fr and larger chest drains (e.g., Seldinger technique or trocar technique). When clinicians desire high flow from a chest drain, they often select a large bore tube. Commercially available stopcocks create a bottleneck in the system when connected to any large bore drain. Imposing a bottleneck in flow negates the benefit of using a drain with a large inner diameter, effectively reducing the flow to the ID of the stopcock instead of the drain ID. The stopcock 12 in this application will reduce the likelihood of a bottleneck for large bore drains up to 24 or 32 Fr. For example, when a drainage catheter having an outer diameter equal to or larger than 16 Fr is connected to the stopcock 12, a flow through the drainage catheter is not reduced to an inner diameter of the stopcock 12.

The disclosed stopcock 12 with 180 degree orientation between barbed fittings/adapters provides a straight and consistent ID from end-to-end, minimizing the likelihood that debris from pleural fluid (e.g., fibrin strands, pus, chyle, thrombi) may become stuck or entrapped, as may be expected with an ID reduction or change in flow direction. 180 degree opposed barbed fittings/adapters with wide bore allow for unimpeded passage of air or fluid, as well as associated tools and instruments such as dilators, obturators, guide wires, rigid or flexible scopes, viscous materials, medical or therapeutic agents.

The outer diameters of the barbed fittings/adapters are selected for compatibility with a variety of tubing commonly connected to chest drains, including tubing that comes with commercially available vacuum pumps, water seals, and dry seals. Such tubing may be silicone, vinyl, or other materials that are more compliant or more rigid. The configuration of the barbed fittings/adapters (e.g., diameters and tapers) are designed to securely contact the ID of any tubing mated to them. This improves sealing and minimizes the need for taping connections. The distance or length of the barbed fittings/adapters is shortened compared to common "Christmas tree" or 5-in-1 connectors. This reduces the overall bulk of the stopcock for benefit to patient comfort. Patients with chest drains are commonly inpatient and in a bed. Larger connections on chest drains are more likely to produce discomfort or injury to the patient if (or when) the patient accidentally lays on the device.

As discussed in greater detail below, in some embodiments, the stopcock 12 may be the only necessary connection between the drain and vacuum unit. The use of a stopcock eliminates the need for multiple adapters and connectors for basic drainage and therapeutic fluid instillation functions or diagnostic sampling. The configuration of the stopcock 12 eliminates the need to connect more than one adapter for draining, sampling fluids, instilling therapeutic fluids, and venting a pneumothorax. The stopcock 12 allows for the drain (e.g., chest drain) and the vacuum tubing to connect at a single hub without sacrificing any functionality of current sets and trays. The reduced quantity of parts in the connection setup reduces the likelihood that components would contact surfaces outside the sterile field. The stopcock is also advantageous for controlling flow or air release after drain placement. To improve the securement of tubing on the barbed adapters of the stopcock 12, the stopcock 12 may be configured to be compatible with clips or other securement devices to limit heavy taping around the drain and simplify maintenance.

The perpendicular connection port 20 (e.g., luer sideport) can allow for instillation of a therapeutic agent or insertion of a pressure monitor, or evacuation or sampling of fluid/air. A standard luer closure may also be attached to maintain hygiene and prevent accidental opening (and patient harm). A luer fitting must necessarily meet industry standards for luer connections, which define ID dimensions and taper characteristics—essentially mandating a bottleneck compared to the ID of any large bore chest drain. Therefore, it is ideal to place the connection port 20 perpendicular to the high-flow pathway between the 180-degree-apart barbed fittings/adapters.

Referring to FIGS. 4-12, embodiments of securement clip designs are provided, which are advantageous for introducing improved and simplified ways to secure drainage tubing and vacuum connections, reducing the possibility of unsecure connections, eliminating the need of using multiple connectors and adapters, and saving time to the drainage procedure. In addition, unlike the tape methods, securement clips allow for a standard of securement to be adopted by users. As a result, a more universal training methodology may be implemented for drain securement.

Figure 4:
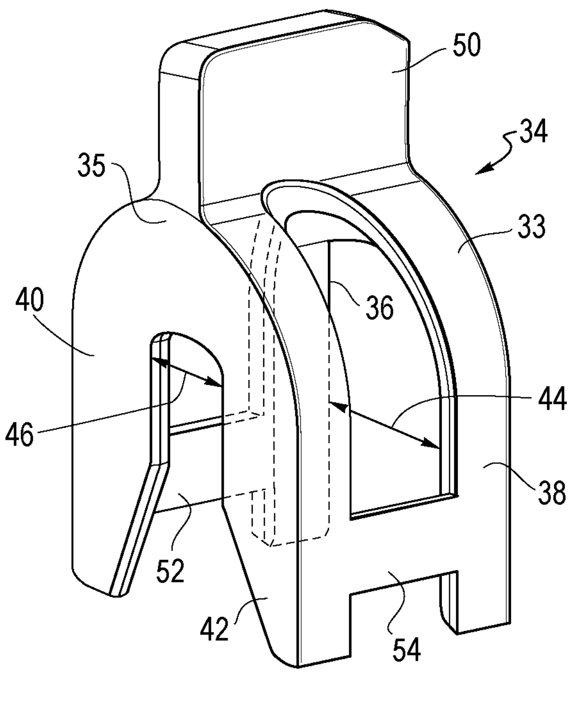
FIG. 4 is a perspective view of a clip according to an embodiment of the present invention.
Figure 5:
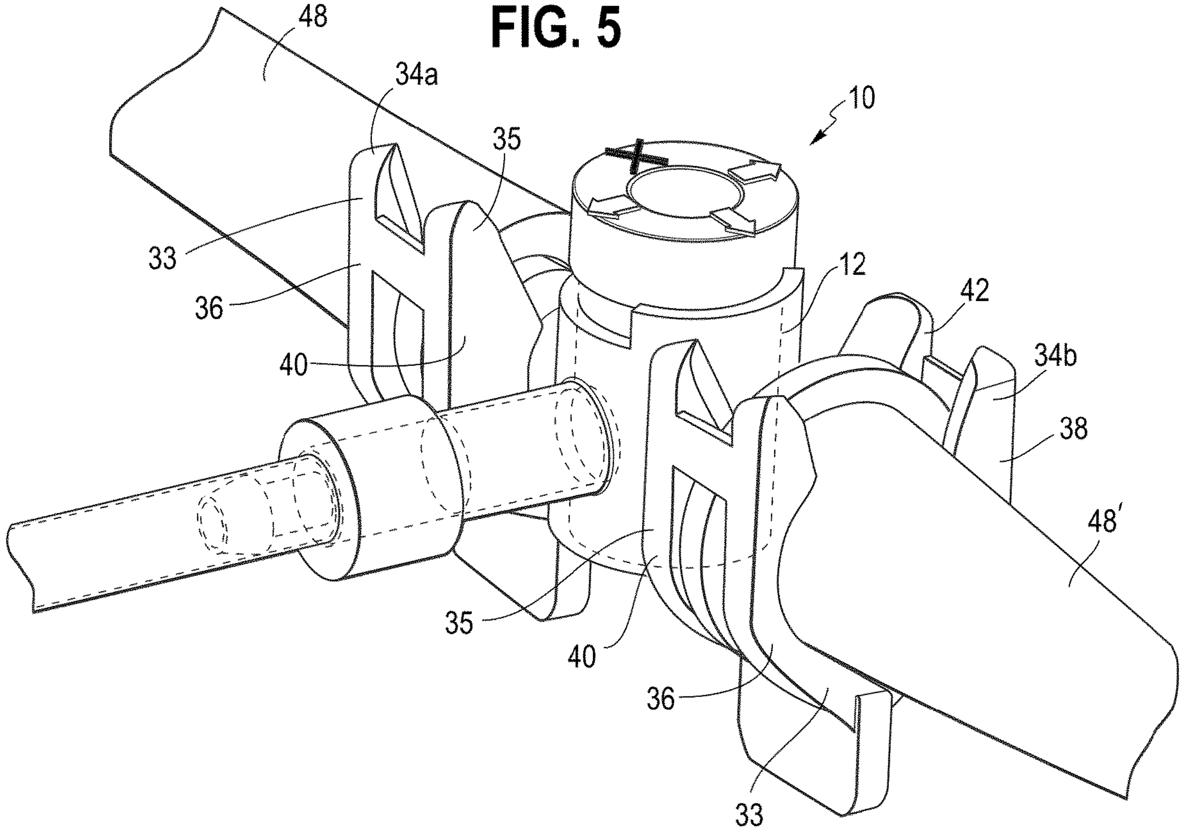
FIG. 5 is a perspective view of a drainage system according to an embodiment of the present invention, including the stopcock of FIG. 1 and two clips of FIG. 4.
Figure 6:
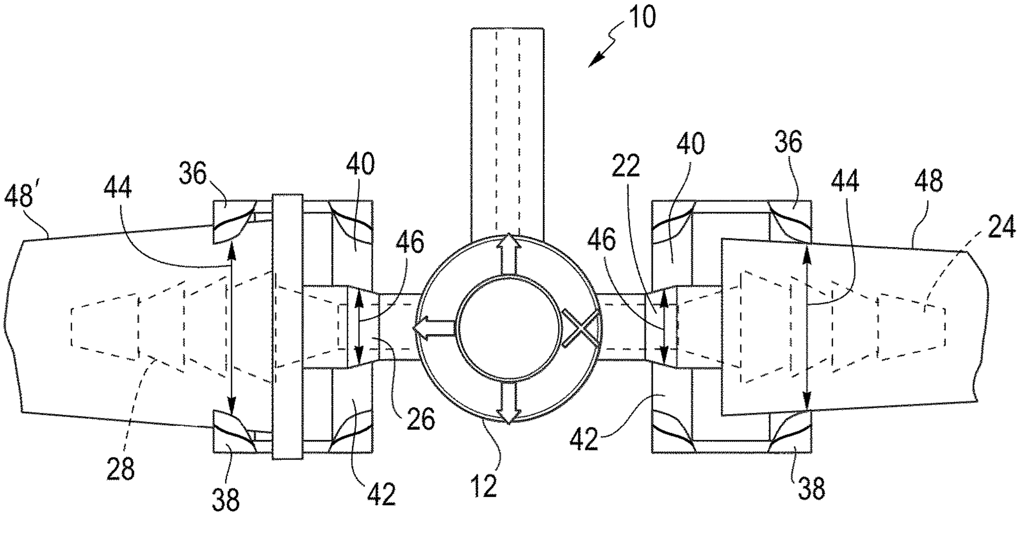
FIG. 6 is a top view of the drainage system of FIG. 5.

Referring to FIGS. 4-6, a first clip 34 may include a first grip 33 and a second grip 35. In some embodiments, the first grip 33 and the second grip 35 each may have a generally arched shape. The first grip 33 includes a first arm 36 and a second arm 38, and the second grip 35 includes a third arm 40 and a fourth arm 42. The first clip 34 may also include a support bar 50 extending between the first grip 33 and the second grip 35. The support bar 50 is configured to strengthen the first clip 34 and establish minimal clip movement after placement. In some embodiments, as shown in FIG. 4, the support bar 50 may extend between the upper portions of the arched shapes of the first grip 33 and the second grip 35, which is advantageous for gripping the first clip 34 and coupling the first clip 34 to a stopcock 12, discussed in greater detail below. In some embodiments, the support bar 50 may include one or more holes for suturing the first clip 34 to a side (e.g., skin) of a patient, thereby further enhancing securement without the need of taping.

In some embodiments, as shown in FIG. 4, the first arm 36 and the third arm 40 may be connected via a first bar 52, and the second arm 38 and the fourth arm 42 may be connected via a second bar 54. As shown, the first bar 52 and the second bar 54 may be coupled to the lower portions of the arched shapes of the first grip 33 and the second grip 35, which is advantageous for securing a drainage catheter or tubing to the barbed stopcock. The configuration (e.g., length, shape) of the support bar 50, the first bar 52, and the second bar 54 may be varied, as desired and/or needed, without departing from the scope of the present invention.

Referring to FIGS. 4-6, the first arm 36 and the second arm 38 may be spaced apart a first distance 44, and the third arm 40 and the fourth arm 42 may be spaced apart a second distance 46. In some embodiments, as shown in FIGS. 5 and 6, the first distance 44 between the first arm 36 and the second arm 38 may be dimensioned such that the first grip 33 fits over (e.g., snugly over) a first tubing (e.g., medical tubing) 48 (e.g., a drainage or vacuum tubing), the second distance 46 between the third arm 40 and the fourth arm 42 may be dimensioned such that the second grip 35 fits over (e.g., snugly over) a second tubing (e.g., medical tubing; a shaft portion 22/26 of a stopcock 12). In some embodiments, the first grip 33 and the second grip 35 may have different sizes, for example, the first distance 44 may be greater than the second distance 46.

The first grip 33 and the second grip 35 may be configured such that the first distance 44 and the second distance 46 may be varied during use (e.g., the grips are made of a flexible material) to accommodate the tubing and stopcock with different sizes. In some embodiments, the first distance 44 may be in the range of about 11 mm-13 mm, for example, the first distance 44 may be about 12 mm. In some embodiments, the second distance 46 may be in the range of about 6.5 mm-8.0 mm, for example, the second distance 46 may be about 7.25 mm.

Referring to FIGS. 5 and 6, a first embodiment of the drainage system 10 is shown. As shown, the first embodiment of the drainage system 10 may include a stopcock 12 and a first clip 34*a*, where the first grip 33 is configured to fit over a first tubing 48 coupled to the first barbed portion 24 of the stopcock 12, and the second grip 35 is configured to fit over the first shaft portion 22 of the stopcock 12, such that the first tubing 48 (e.g., vacuum tubing) is secured to the stopcock 12 via the first clip 34*a*. The first embodiment of the drainage system 10 may also include another first clip 34*b*, where the first grip 33 of the first clip 34*b* is configured to fit over a second tubing 48' (e.g., drainage tubing) coupled to the second barbed portion 28 of the stopcock 12, and the second grip 35 of the first clip 34*b* is configured to fit over the second shaft portion 26 of the stopcock 12, such that the second tubing 48' is also secured to the stopcock 12 via the first clip 34*b*.

The configuration of the first clip 34 and the first embodiment of the drainage system 10 including a stopcock 12 and two first clips 34*a* and 34*b* is advantageous for assisting users with versatility and efficient securement throughout drain care. For example, if a patient needs to be transported, the first tubing 48 (e.g., vacuum tubing) can be easily disconnected without disruption to the connection between the second tubing 48' (e.g., drainage tubing) and the stopcock 12. In addition, the first clip 34 provides users with a cleaner workspace by limiting the use of tape during drain observation and maintenance.

Figure 7:
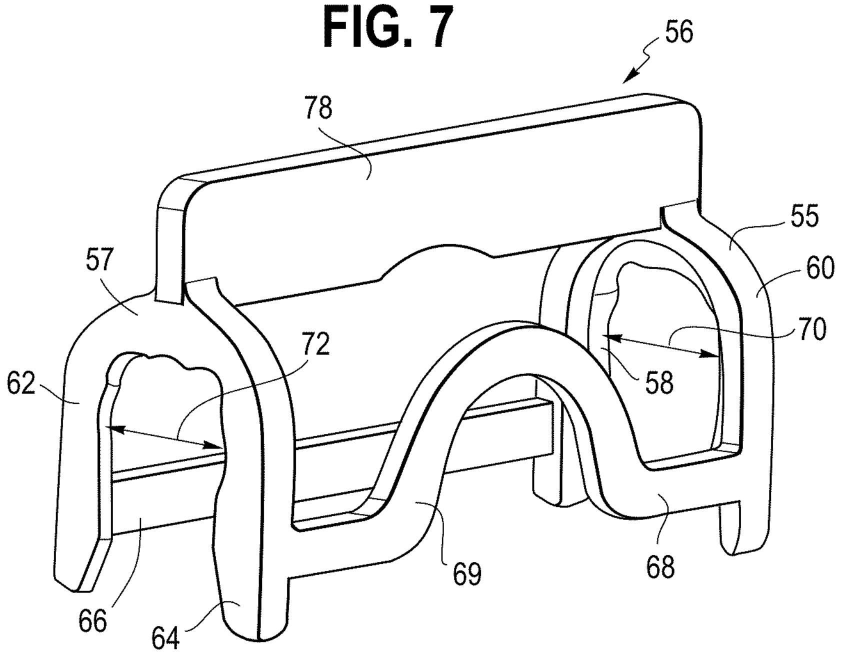
FIG. 7 is a perspective view of a clip according to another embodiment of the present invention.
Figure 12:
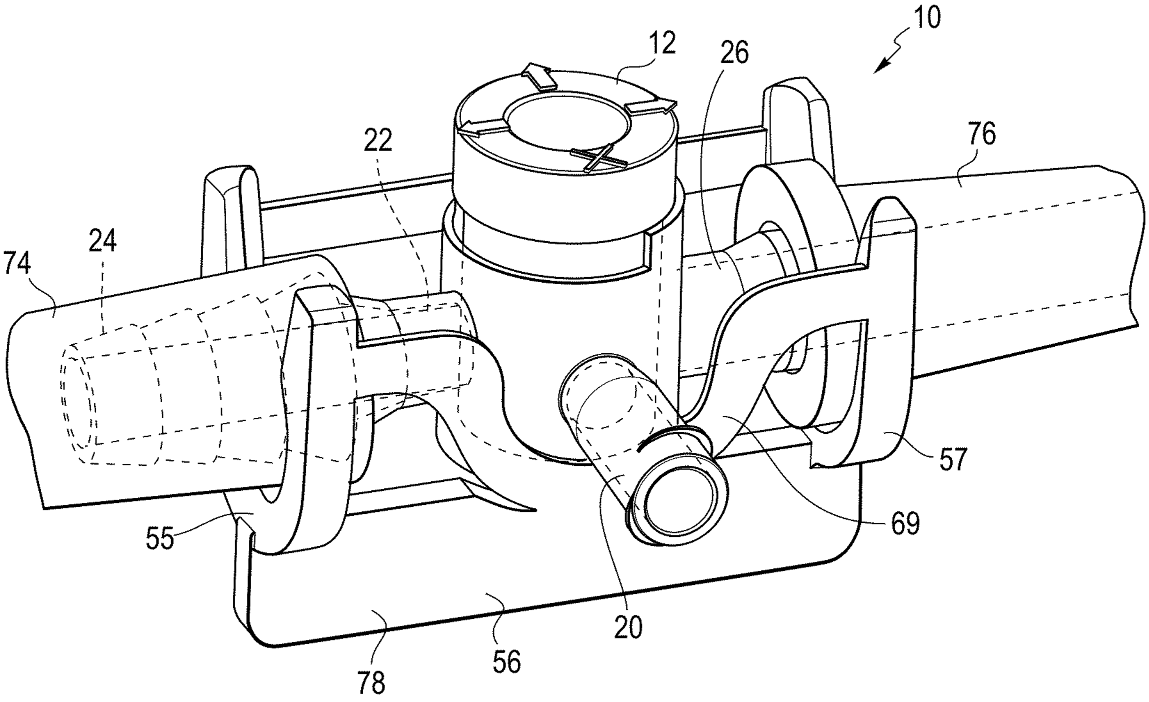
FIG. 12 is another perspective view of the drainage system of FIG. 11, without the cap coupled to the connection port of the stopcock.

Referring to FIGS. 7-12, a second clip 56 may include a first grip 55 and a second grip 57. The first grip 55 and the second grip 57 each may have a generally arched shape. The first grip 55 includes a first arm 58 and a second arm 60, and the second grip 57 includes a third arm 62 and a fourth arm 64. The first arm 58 and the third arm 62 may be connected via a first bar 66, and the second arm 60 and the fourth arm 64 may be connected via a second bar 68. As shown, the second bar 68 may include a bend 69 configured to accommodate the connection port 20 (e.g., a standard luer lock connection) of a stopcock 12. As shown in FIG. 12, for example, the radius of the bend 69 is greater than the radius of the connection port 20. In other words, the projected diameter of the bend 69, if made into a full circle, is greater than the outer diameter of the connection port 20, which allows a user to connect widely available accessories to the stopcock 12. In some embodiments, as shown in FIG. 7, the first bar 66 and the second bar 68 each may be coupled to the lower portions of the arched shapes of the first grip 55 and the second grip 57, which is advantageous for allowing the second clip 56 to perform the same function as two of the first clips 34, but with a single piece.

Figure 8:
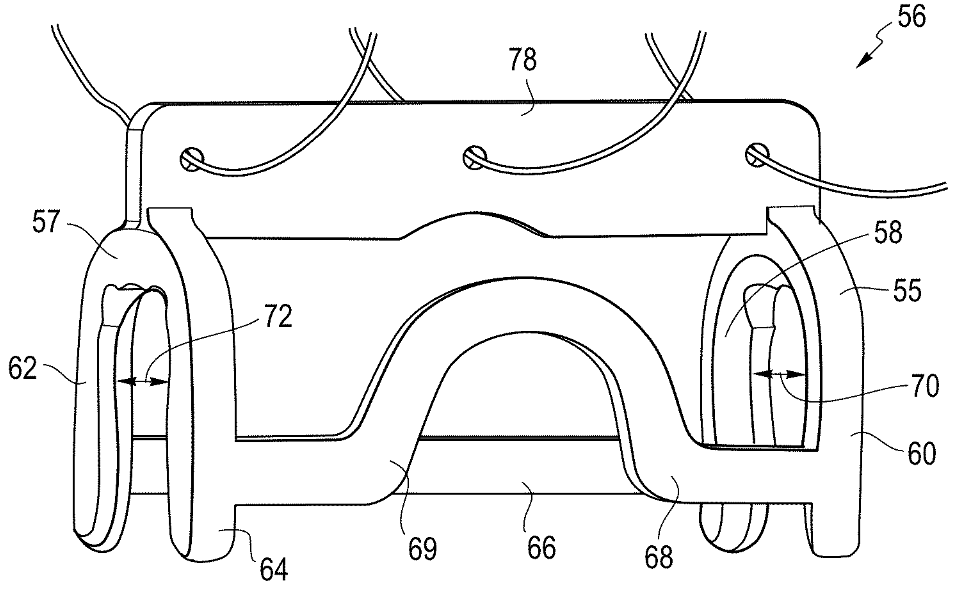
FIG. 8 is a perspective view of a clip according to another embodiment of the present invention.
Figure 9:
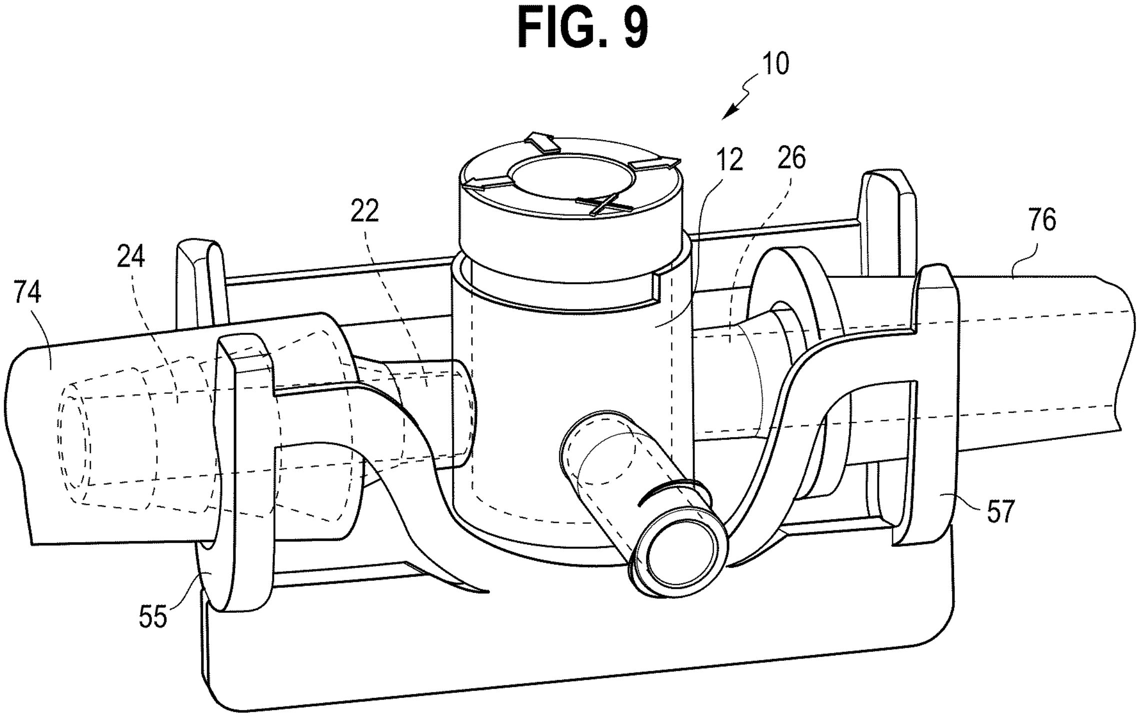
FIG. 9 is a perspective view of a drainage system according to another embodiment of the present invention, including the stopcock of FIG. 1, the clip of FIG. 7, and a first type of tubing coupled to an adaptor of the stopcock.
Figure 10:
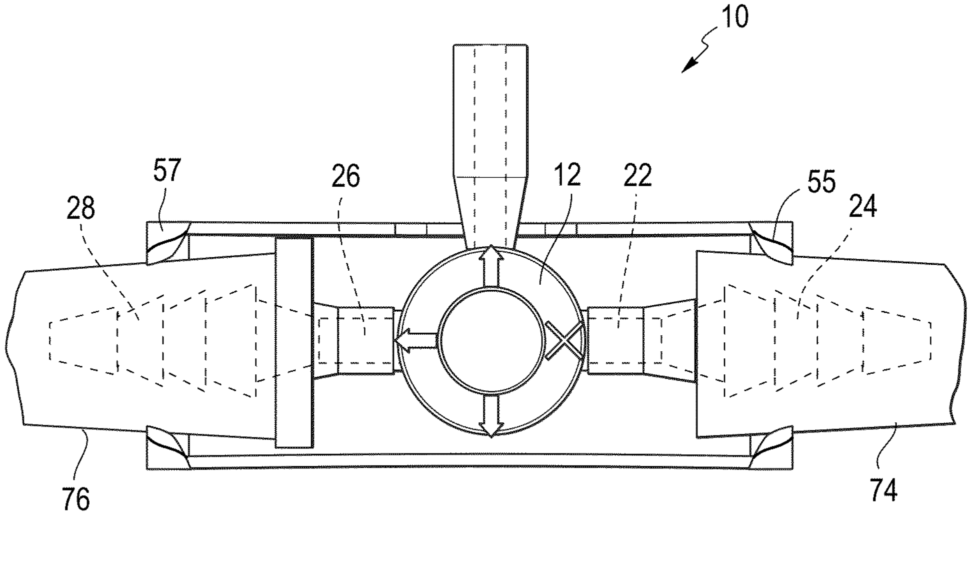
FIG. 10 is a top view of the drainage system of FIG. 9, showing a different orientation of the plug of the stopcock.
Figure 11:
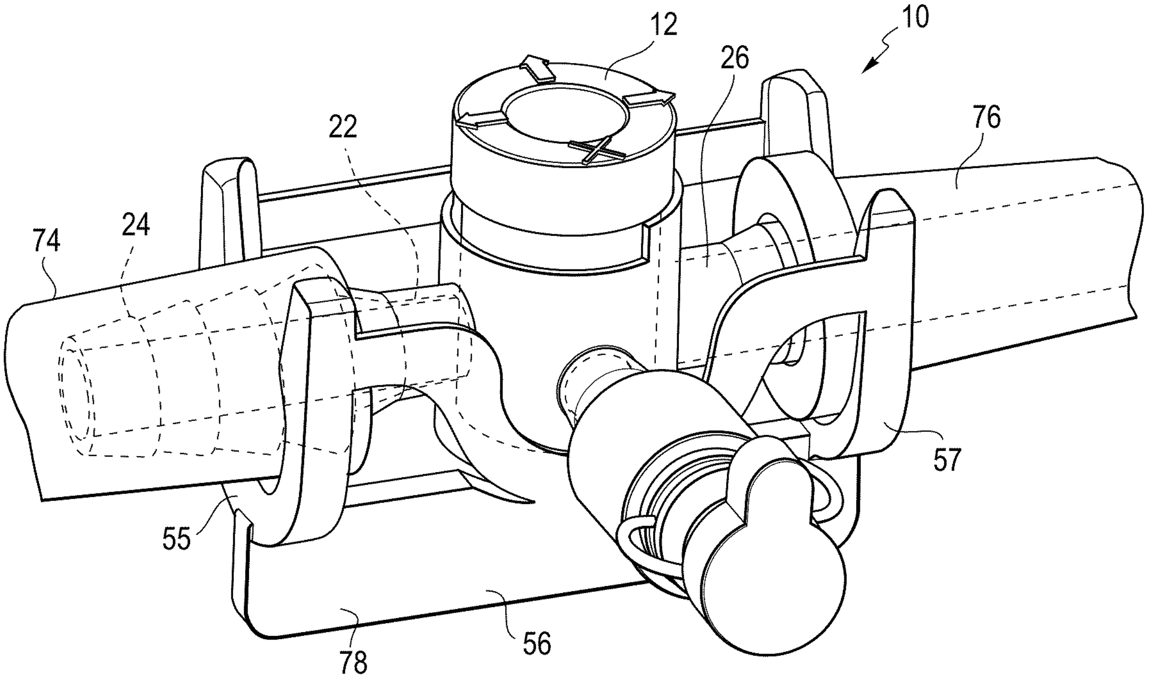
FIG. 11 is another perspective view of the drainage system of FIG. 9, including a second type of tubing coupled to an adaptor of the stopcock and a cap coupled to a connection port of the stopcock.

In some embodiments, the second clip 56 may also include a support bar 78 extending between the first grip 55 and the second grip 57. As shown in FIG. 7, the support bar 78 may extend between the upper portions of the arched shapes of the first grip 55 and the second grip 57, which is advantageous for gripping the second clip 56 and coupling the second clip 56 to a stopcock 12, discussed in greater detail below. In some embodiments, as shown in FIG. 8, the support bar 78 may include one or more holes for suturing the second clip 56 to a side (e.g., skin) of a patient, thereby further enhancing securement without the need of taping. The configuration (e.g., length, shape) of the support bar 78, the first bar 66, and the second bar 68 may be varied, as desired and/or needed, without departing from the scope of the present invention.

In some embodiments, as shown in FIGS. 7-12, the first arm 58 and the second arm 60 are spaced apart a first distance 70, and the third arm 62 and the fourth arm 64 are spaced apart a second distance 72. The first distance 70 is dimensioned such that the first grip 55 fits snugly over a first tubing 74 (e.g., medical tubing), and the second distance 72 is dimensioned such that the second grip 57 fits snugly over a second tubing 76 (e.g., medical tubing). The first medical tubing 74 and the second medical tubing 76 each may be a drainage or vacuum tubing. The first distance 70 may be substantially the same as the second distance 72.

The first grip 55 and the second grip 57 may be configured such that the first distance 70 and the second distance 72 may be varied during use (e.g., the grips are made of a flexible material) to accommodate tubing and stopcock with different sizes. In some embodiments, the first distance 70 and the second distance 72 may be the same, and in the range of about 10.5 mm-12.0 mm.

Referring to FIGS. 9-12, a second embodiment of the drainage system 10' is shown. As shown, the second embodiment of the drainage system 10' may include a stopcock 12 and a second clip 56, where the first grip 55 is configured to fit over a first tubing 74 coupled to the first barbed portion 24 of the stopcock 12, and the second grip 57 is configured to fit over a second tubing 76 coupled to the second barbed portion 28 of the stopcock 12, such that the first tubing 74 and the second tubing 76 are secured to the stopcock 12 via the second clip 56.

The configuration of the second clip 56 is advantageous for providing simplified securement of tubing connections on both ends of the barbed stopcock 12 without the need of using multiple smaller clips. In some embodiments, the first clip 34 and the second clip 56 may each include a tether attachment. The tether may connect on both the clip and the stopcock so that if the clip was taken off the stopcock it would not fall far from the assembly. In other words, even if some parts drop, it would not break the sterility of the part. Adding the clip tether to the larger assembly would also mitigate dropping of the clips after drain placement. The first clip 34 and the second clip 56 each may be made of a soft (yet not pliable) material, without sharp edges or hard materials that cause discomfort and/or harm the patient when they are rolled onto. A variety of softer plastic materials may be considered for the clips to ensure patient comfortability throughout placement. In some embodiments, the first clip 34 and the second clip 56 each may include flat side surfaces, which is advantageous for preventing assembly shifting or disconnection.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A stopcock, comprising:
a base;
a first barbed adapter extending from the base;
a second barbed adapter extending from the base,
wherein the first barbed adapter and the second barbed adapter are substantially 180 degrees apart;
a connection port extending from the base, wherein the connection port is substantially 90 degrees apart from the first barbed adapter and the second barbed adapter; and
a plug disposed in the base, wherein the plug has a substantially cylindrical upper portion, wherein at least one symbol indicating a no-flow position or a flow position is disposed on an upper surface of the upper portion of the plug, wherein at least a portion of the symbol extends between a center of the upper surface and an edge of the upper surface, and wherein the plug includes a blind bore extending from the upper surface of the upper portion of the plug, along a longitudinal axis of the plug, to a position proximate the connection port,
wherein the plug and the base include corresponding detents for locking together,
wherein the stopcock has an inner diameter that is between about 0.2" and about 0.30", and
wherein the stopcock has a substantially same inner diameter from the first barbed adapter to the second barbed adapter with substantially the same inner diameter in the plug when a flow is open to the first and the second barbed adapters.

2. The stopcock of claim 1, wherein the at least one symbol includes a first non-word symbol indicating the no-flow position and a second non-word symbol indicating the flow position.

3. The stopcock of claim 1, wherein the plug includes rounded edges.

4. The stopcock of claim 1, wherein the plug and the base are mated with a semi-circular ridge.

5. The stopcock of claim 1, wherein the stopcock is configured such that when a drainage catheter having an outer diameter equal to or larger than 16 Fr is connected to the stopcock, a flow through the drainage catheter is not reduced to an inner diameter of the stopcock.

* * * * *